United States Patent [19]

Stoneback

[11] 4,316,455
[45] Feb. 23, 1982

[54] METHOD OF DRAPING A SURGICAL PATIENT

[75] Inventor: W. Keith Stoneback, Arlington Heights, Ill.

[73] Assignee: American Hospital Supply Corporation, Evanston, Ill.

[21] Appl. No.: 115,471

[22] Filed: Jan. 25, 1980

[51] Int. Cl.³ .............................................. A61F 13/00
[52] U.S. Cl. ................................................. 128/132 D
[58] Field of Search ................... 128/132 D, 155, 156, 128/157, 292

[56] References Cited

U.S. PATENT DOCUMENTS

| Re. 27,710 | 7/1973 | Melges | 128/132 D |
|---|---|---|---|
| 3,721,234 | 3/1973 | Hadtke et al. | 128/132 D |
| 3,799,161 | 3/1974 | Collins | 128/132 D |
| 3,871,369 | 3/1975 | Krzewinski | 128/132 D |
| 3,881,474 | 5/1975 | Krzewinski et al. | 128/132 D |
| 3,882,859 | 5/1975 | Ericson | 128/132 D |
| 3,916,887 | 11/1975 | Kelly | 128/132 D |
| 3,923,052 | 12/1975 | Zoephel | 128/132 D |
| 4,024,862 | 5/1977 | Collins | 128/132 D |
| 4,041,942 | 8/1977 | Dougan et al. | 128/132 D |
| 4,089,331 | 5/1978 | Hartigan et al. | 128/132 D |

Primary Examiner—John D. Yasko
Attorney, Agent, or Firm—Larry Barger; Mary Jo Kanady

[57] ABSTRACT

A method of draping a surgical patient in which a bottom drape is first attached to a patient, and then a top drape having an opening smaller than the bottom drape is secured by an adhesive to the top surface of the bottom drape to expose a portion of the bottom drape through the top drape's opening. The bottom drape can have the desired shape and size of fenestration, a high degree of liquid repellency, germicidal treatment, etc., while the top drape can be less liquid repellent, giving it a more drapeable, cloth-like characteristic.

8 Claims, 6 Drawing Figures

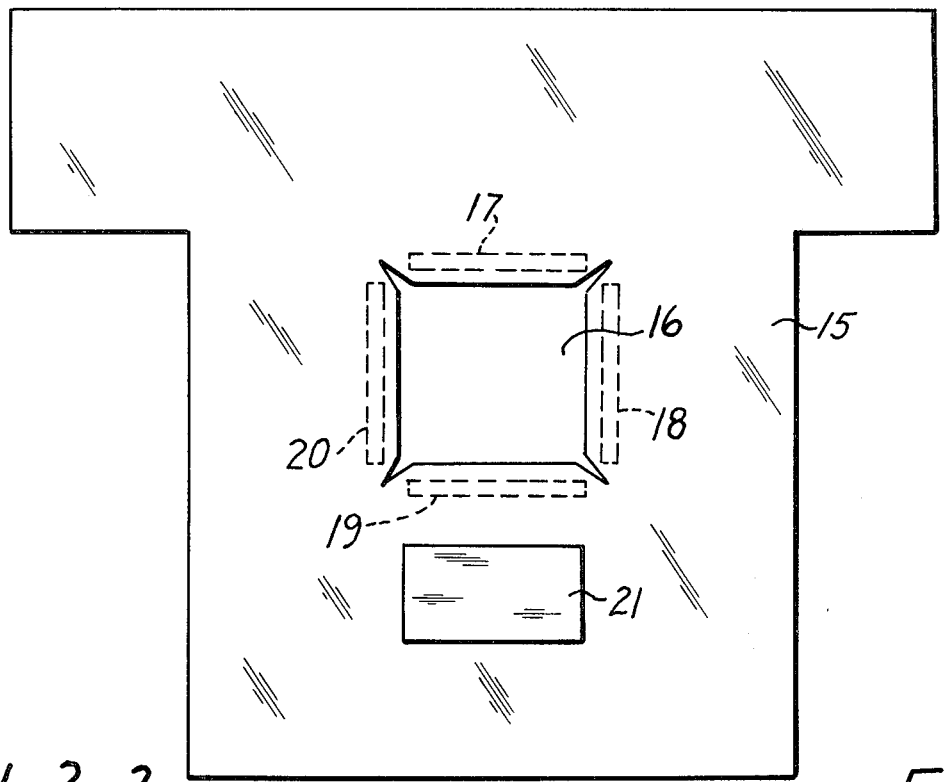
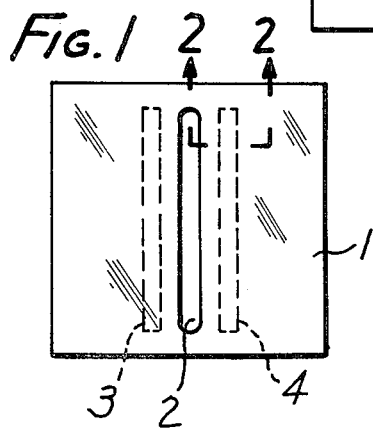
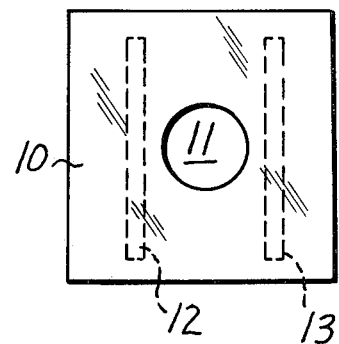
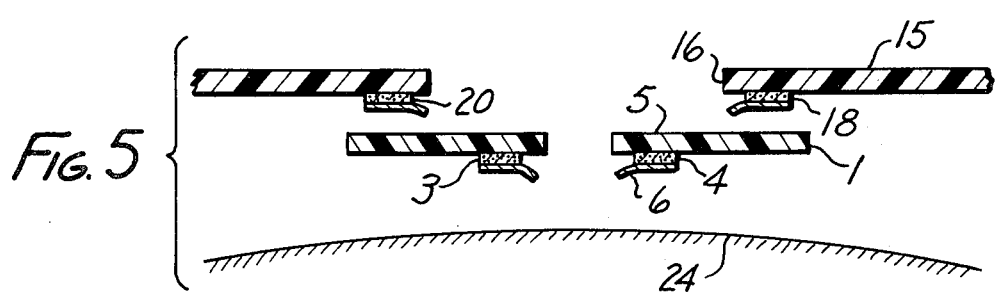
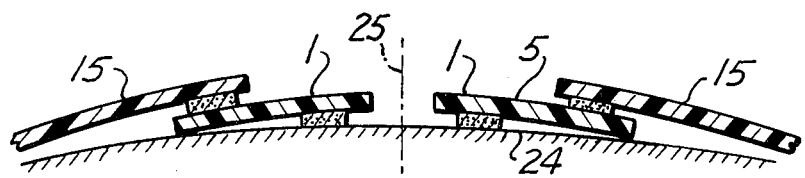

METHOD OF DRAPING A SURGICAL PATIENT

BACKGROUND

Surgical drapes with fenestrations are well-known in the art. In the past, hospitals had to stock many different large size surgical drapes, such as approximately 6'×10' in size, which had different sizes and shapes of fenestrations. The size and shape of the fenestration was dictated by the particular surgical procedure to be performed. Also, most surgical drapes were made out of a single material so that any liquid repellency, biocidal treatment, etc. needed adjacent the fenestration had to be performed over the entire drape. This caused problems in adding to the cost of the drape, plus making the outer portions of the huge drape stiffer and more paper-like because of the liquid repellent treatment. It is desirable to have portions of a surgical drape that are removed from the proximity of the surgical wound to be softer and more drapeable and cloth-like for conforming to other portions of the patient's body and draping from the operating table.

This invention overcomes the above problems by providing a new method of draping a surgical patient. This method includes taking a small bottom drape and securing this bottom drape to a patient. A much larger top drape having an opening smaller than the bottom drape is superimposed on the bottom drape and secured in fixed relationship to the bottom drape. The bottom drape can have the desired size and shape of fenestration, have a high degree of liquid repellency, biocidal treatment, etc. The top drape can be of a softer, more drapeable material that is less liquid repellent than the bottom sheet.

RELATED APPLICATION

Surgical Draping System, filed Jan. 25, 1980., Ser. No. 115,585, by W. Keith Stoneback.

THE DRAWINGS

FIG. 1 is a top plan view of a first embodiment of a bottom drape;

FIG. 2 is an enlarged fragmentary sectional view taken along line 2—2 of FIG. 1;

FIG. 3 is a top plan view of a second embodiment of a bottom drape;

FIG. 4 is a top plan view of a top drape;

FIG. 5 is an exploded sectional view showing the relationship of the patient, bottom drape, and top drape immediately prior to assembly of the draping system; and FIG. 6 is a fragmentary sectional view showing the relationship of the patient, bottom drape, and top drape after assembly of the draping system.

DETAILED DESCRIPTION

In FIG. 1, a bottom drape 1 is shown with an elongated fenestration 2, and this drape has on its bottom surface adhesive strip means 3 and 4 for securing the bottom drape to a patient. FIG. 2 shows the main bottom drape body 1 with a liquid repellent layer 5 on its bottom surface. Layer 5 is laminated to the sheet's main body 1. The lamination can be a coating, or thermoplastic sheet bonded to the bottom surface of sheet 1.

A second embodiment of a bottom drape is shown in FIG. 3. Here bottom drape 10 has a circular fenestration 11 with a pair of adhesive strips 12 and 13 on its bottom surface. Thus, depending on the particular surgical procedure to be performed, either bottom drape 1 or 10 could be selected.

A top drape 15 is shown in FIG. 4 which has an opening 16 that is larger than the fenestration in either drape 1 or drape 10, but is smaller than the outer periphery of such bottom drapes. A series of adhesive strips 17, 18, 19, and 20 on a bottom surface of the top drape surround the opening 16. A slip resistant pad 21 can be secured to a top surface of the top drape for holding medical instruments during an operation. Pad 21 can be of a rubber material.

In draping a surgical patient with the above draping system, the bottom drape 1 is prepared for attachment to the patient by removing protective strip 5 and applying adhesive strips 3 and 4 directly to the patient's skin at the surgical site. Next the top drape 15 is superimposed over the bottom drape 1 so that opening 16 fits entirely within the boundary of the bottom drape, but does not cover any of the bottom drape's fenestration. Next the protective liners are moved from the adhesive strips surrounding opening 16 in the top drape. To aid in removing such protective liners, the corners of opening 16 can be notched or provided with a slit to temporarily fold back flap areas surrounding opening 16 for easier access to the adhesive strips. After the protective liners are removed, the flaps are folded back down and adhesive strips on the top drape firmly secured to an upper surface of the bottom drape. When this has been completed, the entire draping procedure is complete, and a surgical incision can be made on patient 24 at a location such as shown by the dotted line 25.

The above draping procedure permits hospital personnel to select from a group of bottom drapes having a series of different fenestrations, the particular fenestration desired. Then a common top drape can be used with any number of bottom drapes that have different sizes and shapes of fenestrations to create the surgically draped patient. Because of the liquid repellency and other characteristics needed for close proximity to the surgical site, the smaller bottom drape can have a stiffer, more paper-like characteristic. Because it is spaced from direct proximity to the surgical site, the top drape can be of a less liquid repellent, softer, more cloth-like drapeable material. Both the bottom and top drapes can be of a nonwoven, cellulosic material that has the desired properties mentioned above.

In the foregoing description, a specific example has been used to describe the invention. However, those skilled in the art understand that certain modifications can be made to this example without departing from the spirit and scope of the invention.

I claim:

1. A method of draping a surgical patient comprising the steps of:
    (a) securing a bottom drape to a patient;
    (b) placing a top drape having an opening smaller than the bottom drape in superimposed relationship over the bottom drape so that a portion of the bottom drape is exposed through the top drape's opening; and
    (c) securing the top drape in fixed relationship to the bottom drape.

2. A method as set forth in claim 1, wherein the top drape is secured to the bottom drape.

3. A method as set forth in claim 1, wherein the bottom drape has a fenestration smaller than the opening in the top drape.

4. A method as set forth in claim 1, wherein the top drape is secured in fixed relationship to the bottom drape by adhesive means.

5. A method as set forth in claim 4, wherein the securement by adhesive means is between a lower surface of the top drape and an upper surface of the bottom drape.

6. A method as set forth in claim 1, wherein the bottom drape is secured to a patient by adhesive means on a lower surface of the bottom drape.

7. A method of draping a surgical patient comprising the steps of:
(a) securing a bottom drape to a patient with an adhesive means on a lower surface of the bottom drape, which bottom drape has a fenestration;
(b) placing a top drape over the bottom drape, which top drape has an opening smaller than the bottom drape, but larger than the bottom drape's fenestration; and
(c) securing a lower surface of the top drape to an upper surface of the bottom drape by adhesive means.

8. A method of draping a surgical patient comprising the steps of:
(a) removing from a group of bottom drapes having different fenestrations a single bottom drape with a fenestration;
(b) securing the bottom drape to a patient;
(c) removing a single top drape from a group of top drapes each having an opening of a common size and shape, said opening in the top drape being smaller than the bottom drape, but larger than the bottom drape's fenestration;
(d) placing the top drape in superimposed relationship over the bottom drape so that a portion of the bottom drape is exposed through the top drape's opening; and
(e) securing the top drape to the bottom drape.

* * * * *